US011484520B2

(12) United States Patent
Lopez Vales et al.

(10) Patent No.: US 11,484,520 B2
(45) Date of Patent: Nov. 1, 2022

(54) SPECIALIZED PRO-RESOLVING LIPID MEDIATORS FOR USE IN THE TREATMENT OF NEURODEGENERATIVE DISEASES AND/OR AUTOIMMUNE DISEASES

(71) Applicant: UNIVERSITAT AUTONOMA DE BARCELONA, Bellaterra (ES)

(72) Inventors: Ruben Lopez Vales, Bellaterra (ES); Alba Sanchez Fernandez, Bellaterra (ES); Anna Martinez Muriana, Bellaterra (ES); Isaac Francos-Quijorna, London (GB)

(73) Assignee: UNIVERSITAT AUTONOMA DE BARCELONA, Bellaterra (ES)

( * ) Notice: Subject to any disclaimer, the term of this patent is extended or adjusted under 35 U.S.C. 154(b) by 261 days.

(21) Appl. No.: 16/478,740

(22) PCT Filed: Jan. 17, 2018

(86) PCT No.: PCT/EP2018/051076
§ 371 (c)(1),
(2) Date: Jul. 17, 2019

(87) PCT Pub. No.: WO2018/134230
PCT Pub. Date: Jul. 26, 2018

(65) Prior Publication Data
US 2020/0038356 A1 Feb. 6, 2020

(30) Foreign Application Priority Data
Jan. 18, 2017 (EP) .................. 17151909.3

(51) Int. Cl.
A61K 31/202 (2006.01)
A61K 8/365 (2006.01)
A23L 33/10 (2016.01)
A61P 25/28 (2006.01)
A61K 9/00 (2006.01)

(52) U.S. Cl.
CPC ............ *A61K 31/202* (2013.01); *A23L 33/10* (2016.08); *A61K 8/365* (2013.01); *A61P 25/28* (2018.01); *A61K 9/0053* (2013.01)

(58) Field of Classification Search
CPC .... A61K 31/202; A61K 8/365; A61K 9/0053; A23L 33/10; A61P 25/28
USPC ........................................................ 514/560
See application file for complete search history.

(56) References Cited

U.S. PATENT DOCUMENTS

| 5,441,951 | A | 8/1995 | Serhan |
| 8,927,747 | B2 | 1/2015 | Serhan et al. |
| 9,340,483 | B2 | 5/2016 | Gjorstrup |
| 9,416,118 | B2 | 8/2016 | Serhan et al. |
| 9,463,177 | B2 | 10/2016 | Serhan et al. |
| 10,154,977 | B2 | 12/2018 | Serhan et al. |
| 10,653,703 | B2 | 5/2020 | Serhan et al. |
| 2005/0075398 | A1 | 4/2005 | Bazan et al. |
| 2013/0302343 | A1 | 11/2013 | Becher et al. |
| 2015/0018417 | A1* | 1/2015 | Freeman ................... A61P 1/04 514/560 |
| 2015/0126602 | A1* | 5/2015 | Bannenberg ............. A61P 1/16 514/560 |
| 2016/0367510 | A1* | 12/2016 | Mathisen .................. A23L 2/02 |
| 2020/0163923 | A1 | 5/2020 | Lopez Vales et al. |

FOREIGN PATENT DOCUMENTS

| CN | 102021075 A | 4/2011 |
| WO | WO 2013/170006 | * 11/2013 |
| WO | WO 2019016580 | 1/2019 |

OTHER PUBLICATIONS

Abdulnour, R.E., et al., "Maresin 1 biosynthesis during platelet-neutrophil interactions is organ-protective," *PNAS* 111(46):16526-16531, National Academy of Sciences, United States (2014).
Akagi, D., et al., "Systemic delivery of proresolving lipid mediators resolvin D2 and maresin 1 attenuates intimal hyperplasia in mice," *FASEB Journal* 29(6):2504-2513, Federation of American Societies for Experimental Biology, United States (2015).
Arnold, L., et al., "Inflammatory monocytes recruited after skeletal muscle injury switch into antiinflammatory macrophages to support myogenesis," *The Journal of Experimental Medicine* 204(5):1057-1069, Rockefeller University Press, United States (2007).
Basso, D.M.. et al., "Basso Mouse Scale for Locomotion Detects Differences in Recovery after Spinal Cord Injury in Five Common Mouse Strains," Journal of Neurotrauma 23(5):635-659, Mary Ann Liebert, United States (2006).
Batchelor, P.E., et al., "Comparison of inflammation in the brain and spinal cord following mechanical injury," *Journal of Neurotrauma* 25(10):1217-1225, Mary Ann Liebert, United States (2008).
Bazan, N.G., "Neuroprotectin D1-mediated anti-inflammatory and survival signaling in stroke, retinal degenerations, and Alzheimer's disease," *Journal of Lipid Research* 50: S400-S405, Americal Society for Biochemistry and Molecular Biology, United States (2009).
Bazan, N.G., et al., "Novel aspirin-triggered neuroprotectin D1 attenuates cerebral ischemic injury after experimental stroke," *Experimental Neurology* 236(1):122-130, Elsevier, Netherlands (2012).
Buckley, C.D,, et al., "Pro-resolving lipid mediators and mechanisms in the resolution of acute inflammation," *Immunity* 40(3):315-327, Cell Press, United States (2014).
Coll-Miró, M., et al., "Beneficial effects of IL-37 after spinal cord injury in mice," *Proc. Natl. Acad. Sci.* 113(5):1411-1416, National Academy of Science, United States (2016).

(Continued)

*Primary Examiner* — Yevgeny Valenrod
(74) *Attorney, Agent, or Firm* — Sterne, Kessler, Goldstein & Fox P.L.L.C.

(57) ABSTRACT

The present invention relates to a specialized pro-resolving lipid mediator comprising maresins, D-series resolvins, E-series resolvins, protectins or lipoxins, or a combination thereof, for use in the treatment of neurodegenerative diseases and/or autoimmune diseases.

21 Claims, 3 Drawing Sheets
Specification includes a Sequence Listing.

(56) References Cited

OTHER PUBLICATIONS

Crane, P.K., et al., "Association of Traumatic Brain Injury with Late-Life Neurodegenerative Conditions and Neuropathologic Findings," *JAMA Neurol* 73(9):1062-1069, American Medical Association, United States (2016).
Cudkowicz, M.E., et al., "Trial of Celecoxib in Amyotrophic Lateral Sclerosis," *Ann. Neurol.* 60(1):22-31, Wiley Periodicals, United States (2006).
Dalli, J., et al., "The novel 13S, 14S-epoxy-maresin is converted by human macrophages to maresin 1 (MaR1), inhibits leukotriene A4 hydrolase (LTA4H), and shifts macrophage phenotype," *FASEB Journal* 27(7):2573-2583, Federation of American Societies for Experimental Biology, United States (2013).
David, S., et al., "Repertoire of microglial and macrophage responses after spinal cord injury," *Nature Reviews Neuroscience* 12(7):388-399, Macmillan Publishers Limited, England (2011).
David, S., et al., "Harmful and beneficial effects of inflammation after spinal cord injury: potential therapeutic implications," *Handbook of Clinical Neurology* 109(3):485-502, Elsevier, Netherlands (2012).
David, S., et al., "Role of phospholipase A2s and lipid mediators in secondary damage after spinal cord injury," *Cell Tissue Res* 349(1):249-267, Springer, United States (2012).
David, S., et al., "Macrophage and Microglial Plasticity in the Injured Spinal Cord," *Neuroscience* 307:311-318, Elsevier, Netherlands (2015).
Deng, B., et al., "Maresin Biosynthesis and Identification of Maresin 2, a New Anti-Inflammatory and Pro-Resolving Mediator from Human Macrophages," *PLoS ONE* 9(7):1-9, Public Library of Science, United States (2014).
Fawcett, J.W., et al., "Defeating inhibition of regeneration by scar and myelin components," *Handbook of Clinical Neurology* 109(3):503-522, Elsevier, Netherlands (2012).
Francos-Quijorna, I., et al., "IL-4 drives microglia and macrophages toward a phenotype conductive for tissue repair and functional recovery after spinal cord injury," *GLIA* 64(12):2079-2092, Wiley Periodicals, United States (2016).
Francos-Quijorna, I., et al., "Maresin-1 Promotes Inflammatory Resolution, Neuroprotection and Functional Neurological Recovery After Spinal Cord Injury," *The Journal of Neuroscience* 37(48):11731-11743, Society for Neuroscience, United States (2017).
Gomez-Nicola, D. et al., "Microglial dynamics and role in the healthy and diseased brain: a paradigm of functional plasticity," *The Neuroscientist* 21(2):169-184, SAGE Publications, United States (2015).
Guanghao, L., et al., "Neuronal phagocytosis by inflammatory macrophages in ALS spinal cord: inhibition of inflammation by resolving D1," *American Journal of Neurodegenerative Disease,* 1(1):60-74, e-Century Publishing, United States (2012).
Harrison, J.L., et al., "Resolvins AT-D1 and E1 differentially impact functional outcome, post-traumatic sleep, and microglial activation following diffuse brain injury in the mouse," *Brain Behavior, and Immunity* 47:131-140, Elsevier, Netherlands (2015).
Hassan, I.R., et al., "Acute Changes in Dietary w-3 and w-6 Polyunsaturated Fatty Acids Have a Pronounced Impact on Survival following Ischemic Renal Injury and Formation of Renoprotective Docosahexaenoic Acid-Derived Protectin D1," *The Journal of Immunology* 182(5):3223-3232, American Association of Immunologists, United States (2009).
Hawthorne, A.L., et al., "Emerging concepts in myeloid cell biology after spinal cord injury", Neurotherapeutics: *The Journal of the American Society for Experimental NeuroTherapeutics* 8(2):252-261, The American Society for Experimental NeuroTherapeutics, United States (2011).
Huang, W.L., et al., "A combination of intravenous and dietary docosahexaenoix acid significantly improves outcome after spinal cord injury," *Brain* 130(Pt 11):3004-3019, Oxford University Press, England (2007).
International Search Report and Written Opinion for International Application No. PCT/IB2017/054398, Unite States Patent and Trademark Office, United States, dated Nov. 17, 2017, 10 pages.
King, V.R., et al., "Omega-3 Fatty Acids Improve Recovery, whereas Omega-6 Fatty Acids Worsen Outcome, after Spinal Cord Injury in the Adult Rat," *The Journal of Neuroscience* 26(17):4672-4680, Society for Neuroscience, United States (2006).
Kroner, A., et al., "TNF and increased intracellular iron after macrophage polarization to a detrimental M1 phenotype in the injured spinal cord," *Neuron* 83(5):1098-1116, Cell Press, United States (2014).
Lopez-Vales, R,. et al., "Fenretinide promotes functional recovery and tissue protection after spinal cord contusion injury in mice," *The Journal of Neuroscience* 30(9):3220-3226, Society for Neuroscience, United States (2010).
Lu, Y., et al., "Signaling regulations of neuronal regenerative ability," *Current Opinion in Neurobiology* 27:135-142, Elsevier, Netherlands (2014).
Macron, R., et al., "Maresin 1, a proresolving lipid mediator derived from omega-3 polyunsaturated fatty acids, exerts protective actions in murine models of colitis," *The Journal of Immunology* 191(8):4288-4298, American Association of Immunologists, United States (2013).
Marcheselli, V.L., et al., "Novel docosanoids inhibit brain ischemia-reperfusion-mediated leukocyte infiltration and pro-inflammatory gene expression," *The Journal of Biological Chemistry* 278(44):43807-43817, The American Society for Biochemistry and Molecular Biology, United States (2003).
Michael-Titus, A.T., et al., "Omega-3 fatty acids and traumatic neurological injury: from neuroprotection to neuroplasticity?," *Trends in Neurosciences* 37(1):30-38, Cell Press, United States (2014).
Murray, P.J., et al., "Macrophage activation and polarization: nomenclature and experimental guidelines," *Immunity* 41(1):14-20, Cell Press, United States (2014).
Nahrendorf, M., et al., "The healing myocardium sequentially mobilizes two monocyte subsets with divergent and complementary functions," *The Journal of Experimental Medicine* 204(12):3037-3047, Rockefeller University Press, United States (2007).
Popovich, P.G., et al., "Can the immune system be harnessed to repair the CNS?," *Nature Reviews Neuroscience* 9(6):481-493, Nature Publishing Group, England (2008).
Popovich, P.G., "Neuroimmunology of traumatic spinal cord injury: A brief history and overview," *Experimental Neurology* 258:1-4, Elsevier, Netherlands (2014).
Prüss, H., et al., "Non-resolving aspects of acute inflammation after spinal cord injury (SCI): indices and resolution plateau," *Brain Pathology* 21(6):652-660, International Society of Neuropathology, United States (2011).
Quijorna, I.F., "Activation of inflammatory resolution programs as a new therapeutic approach to promote neuroprotection after SCI," *Universitat Autònoma de Barcelona,* 1-257, Spain (Jul. 22, 2016).
Santos-Nogueira, E., et al., "Activation of Lysophosphatidic Acid Receptor Type 1 Contributes to Pathophysiology of Spinal Cord Injury," *The Journal of Neuroscience* 35 (28):10224-10235), Society for Neuroscience, United states (2015).
Serhan, C.N., et al., "Maresins: novel macrophage mediators with potent antiinflammatory and proresolving actions," *The Journal of Experimental Medicine* 206(1):15-23, Rockefeller University Press, United States (2009).
Serhan, C.N., et al., "Macrophage proresolving mediator maresin 1 stimulates tissue regeneration and controls pain," *FASEB Journal* 26(4):1755-1765, Federation of American Societies for Experimental Biology, United States (2012).
Serhan, C.N., "Pro-resolving lipid mediators are leads for resolution physiology," *Nature* 510:92-101, Macmillan Publishers Limited, England (2014).
Serhan, C.N. et al., "Protectins and maresins: New pro-resolving families of mediators in acute inflammation and resolution bioactive metabolome," *Biochim Biophys Acta* 1851(4):397-413, Elsevier, Netherlands (2015).
Schawanke, R.C. et al., "EPA- and DHA-derived resolvins' actions in inflammatory bowel disease," *European Journal of Pharmacology* 785:156-164, Elsevier, Netherlands (2015).

(56) References Cited

OTHER PUBLICATIONS

Schwab, J.M., et al., "Resolvin E1 and protectin D1 activate inflammation-resolution programs," *Nature* 510(7503):92-101, Nature Publishing Group, England (2007).
Steinman, L., "No quiet surrender: molecular guardians in multiple sclerosis brain," *The Journal of Clinical Investigation* 125(4):1371-1378, American Society for Clinical Investigation, United States (2015).
Stenudd, M., et al., "Role of endogenous neural stem cells in spinal cord injury and repair," *JAMA Neurology* 72(2):235-237, American Medical Association, United States (2015).
Svensson, C.I., et al., "Lipoxins and aspirin-triggered lipoxin inhibit inflammatory pain processing," *The Journal of Experimental Medicine* 204(2):245-252, Rockefeller University Press, United States (2007).
Tian, Y., et al., "Resolvin D2 recovers neural injury by suppressing inflammatory mediators expression in lipopolysaccharide-induced Parkinson's disease rat model," *Biochemical and Biophysical Research Communications* 460(3):799-805, Elsevier, Netherlands (2015).
"TNF neutralization in MS: Results of a randomized, placebo-controlled multicenter study," The Lenercept Multiple Sclerosis Study Group and The University of British Columbia MS/MRI Analysis Group, *Neurology* 53(3):457-465, American Academy of Neurology, United States (1999).
Xian, W., et al., "The pro-resolving lipid mediator Maresin 1 protects against cerebral ischemia/reperfusion injury by attenuating the pro-inflammatory response," *Biochemical and Biophysical Research Communications* 472(1):175-181, Elsevier, Netherlands (2016).
Zhu, M., et al., "Pro-Resolving Lipid Mediators Improve Neuronal Survival and Increase AB42 Ohagocytosis," *Mol Neurobiol* 53(4):1-32, Springer, United States (2016).

* cited by examiner

SPECIALIZED PRO-RESOLVING LIPID MEDIATORS FOR USE IN THE TREATMENT OF NEURODEGENERATIVE DISEASES AND/OR AUTOIMMUNE DISEASES

REFERENCE TO SEQUENCE LISTING SUBMITTED ELECTRONICALLY VIA EFS-WEB

The content of the electronically submitted sequence listing (Name: 4453-0010001_SL_ST25.TXT; Size: 606 bytes; and Date of Creation: Jan. 30, 2020) filed with the application is incorporated herein by reference in its entirety.

FIELD OF THE INVENTION

The present patent application is the U.S. national phase application of International Application No. PCT/EP2018/051076, filed on Jan. 17, 2018, which claims the priority of European patent application EP17151909.3, filed on Jan. 18, 2017, both of which are hereby incorporated by reference in their entireties.

The present invention relates to the field of neurodegenerative and/or autoimmune diseases. More particularly, the present invention relates to specialized pro-resolving lipid mediators, preferably maresin, and compositions comprising thereof, for use in the treatment of neurodegenerative and/or autoimmune diseases, preferably Multiple Sclerosis (MS) and Amyotrophic Lateral Sclerosis (ALS).

BACKGROUND OF THE INVENTION

Neurodegenerative disease is an umbrella term for a range of conditions which primarily affect the neurons in the human brain. Neurons are the building blocks of the nervous system which includes the brain and spinal cord. Neurons normally do not reproduce or replace themselves, so when they become damaged or die they cannot be replaced by the body. Examples of neurodegenerative diseases include Parkinson's, Alzheimer's, amyotrophic lateral sclerosis and Huntington's disease. Neurodegenerative diseases are incurable and debilitating conditions that result in progressive degeneration and/or death of nerve cells. This causes problems with movement (called ataxias), or mental functioning (called dementias).

Likewise, immune system disorders or autoimmune diseases cause abnormally low activity or over activity of the immune system. Immune deficiency diseases decrease the body's ability to fight invaders, causing vulnerability to infections. In cases of immune system over activity, the body attacks and damages its own tissues. This is the case of autoimmune diseases, in which the immune system produces antibodies that instead of fighting infections, attack the body's own tissues elements. Treatment for autoimmune diseases generally focuses on reducing immune system activity. Examples of autoimmune diseases include: Rheumatoid arthritis, Systemic lupus erythematosus (lupus), Inflammatory bowel disease (IBD), Multiple sclerosis (MS), Type 1 diabetes mellitus, Guillain-Barre syndrome, Chronic inflammatory demyelinating polyneuropathy, Psoriasis, Graves' disease, Hashimoto's thyroiditis, Myasthenia gravis, Vasculitis.

Despite neurodegenerative and autoimmune diseases have different etiology, it is well known that the inflammatory response localized in the Central Nervous System has a crucial role for the pathogenesis of these diseases.

Nowadays, there are numerous research groups all over the world looking for complete or palliative solutions to the long list of these diseases since the population affected by these diseases is continuously growing, in particular, due to the current longer life expectancy.

With this goal, the present inventors have surprisingly found that some molecules called "Specialized pro-resolving lipid mediator" or "SPM" are useful in the treatment of such diseases.

"Specialized pro-resolving lipid mediator" (SPM, also termed specialized pro-resolving mediators) are a large and growing class of cell signaling molecules formed in cells by the metabolism of polyunsaturated fatty acids (PUFA) by one or a combination of lipoxygenase, cyclooxygenase, and cytochrome P450 monooxygenase enzymes. Preclinical studies, primarily in animal models and human tissues, implicate SPM in orchestrating the resolution of inflammation. These studies suggest that synthetic SPM that are resistant to being metabolically inactivated hold promise of being clinically useful pharmacological tools for preventing and resolving a wide range of pathological inflammatory responses along with the tissue destruction and morbidity that these responses cause. These molecules include maresins, D-series resolvins, E-series resolvins, protectins and lipoxins. Lipoxins are derived from arachidonic acid, E-series resolvins are derived from the long-chain n-3 fatty acid eicosapentaenoic acid (EPA) and D-series resolvins, protectins/neuroprotectins and maresins, are all derived from the n-3 fatty acid docosahexaenoic acid (DHA). There is mounting evidence for the role of these compounds in inflammation processes.

For example, WO2012/170791 discloses mono and dihydroxy analogues of docosahexaenoic acid (DHA) used in the treatment or prevention of inflammation processes. WO 2010/033509 discloses 14-hydroxy analogues of docosahexaenoic acid (DHA) used in the treatment or prevention of inflammation processes. WO2012/135032 discloses particles generated at least in part from cellular-derived microparticles have anti-inflammatory properties and can be used as drug delivery systems to treat, for example, inflammation, wounds, or pain, being said particles resolvins, lipoxins, maresins and protectins, among others. Serhan et al., "Pro-resolving lipid mediators are leads for resolution physiology", Nature, Vol. 10, p. 92-101, 5 Jun. 2014, discloses SPMs and their implication in inflammation processes. WO 2013/170006 discloses Specialized Pro-resolving Mediators (SPMs) and SPM precursors obtained from natural sources (oils), and their use in nutritional supplements and pharmaceutical and cosmetic formulations for ameliorating inflammation and diseases having an inflammatory component.

As shown above, it is well known the use of SPMs as anti-inflammatory agents, but the present inventors have surprisingly found that these molecules, in particular maresin, are also useful in the treatment of neurodegenerative diseases and/or autoimmune diseases, in particular in the treatment of multiple sclerosis and amyotrophic lateral sclerosis. This is very advantageous because there are agents currently used as anti-inflammatory drugs which are not useful or even negatively affect patients suffering from neurodegenerative diseases and/or autoimmune diseases, in particular multiple sclerosis and amyotrophic lateral sclerosis. Examples thereof are Enbrel® (etanercept) or Celebrex® (celecoxib) and further evidence is also found in the articles: "TNF neutralization in MS Results of a randomized, placebo-controlled multicenter study" developed by The Lenercept Multiple Sclerosis Study Group and The University of British Columbia MS/MRI Analysis Group and published in Neurology (1999, pages 457-507); and "Trial of Celecoxib in Amyotrophic Lateral Sclerosis" by Cudkowicz et al., Ann. Neurol. 2006; 60: 22-31.

Accordingly, no reference is found in the literature for the direct use of these compounds for the purposes disclosed herein.

BRIEF DESCRIPTION OF THE DRAWINGS

FIG. 1A shows an assessment of locomotor loss in EAE mice over time. Note that treatment with Maresin at disease onset led to significant amelioration of locomotor deficits (*p<0.05 vs vehicle; Two-way repeated measurements ANOVA with Bonferroni post-hoc test). FIG. 1B shows a histological assessment of myelin loss in the spinal cord assess from LUXOL® fast blue stained tissue sections. Maresin resulted in significant protection against demyelination (*p<0.037 vs vehicle; t-test).

FIG. 2A shows an electrophysiological test showing preservation of the compound muscle action potential (CMAP) in tibialis anterior (TA) muscle. Note that Maresin delayed the loss of CMAP amplitude in 4 weeks (*p<0.05 vs vehicle; Two-way repeated measurements ANOVA with Bonferroni post-hoc test). FIG. 2B shows that treatment with Maresin leads to significant preservation in functional outcomes assessed by the rotarod test (*p=0.017; Matel-Cox test).

SUMMARY OF THE INVENTION

Figures 1A, 1B:
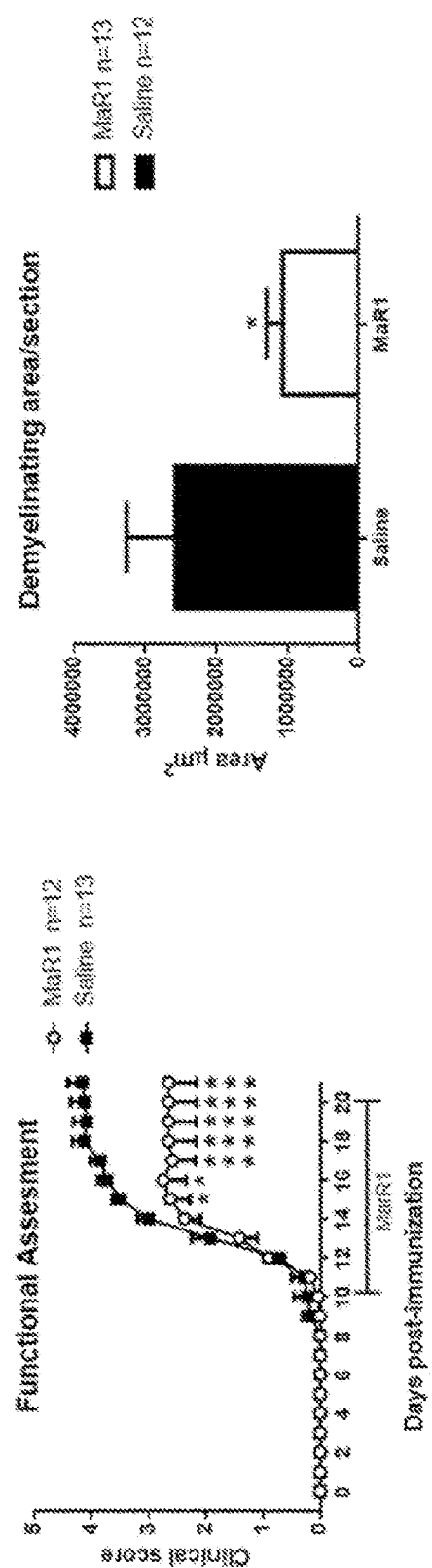
FIG. 1A and FIG. 1B show therapeutic effects of Maresin in an Experimental Autoimmune Encephalomyelitis (EAE), a mouse model of multiple sclerosis.

The present invention relates to a specialized pro-resolving lipid mediator comprising maresins, D-series resolvins, E-series resolvins, protectins or lipoxins, or a combination thereof, for use in the treatment of neurodegenerative diseases and/or autoimmune diseases.

The present invention further relates to a composition comprising a specialized pro-resolving lipid mediator selected from the group consisting of maresins, D-series resolvins, E-series resolvins, protectins and lipoxins, or a combination thereof, for use in the treatment of neurodegenerative diseases and/or autoimmune diseases.

DETAILED DESCRIPTION OF THE INVENTION

The present invention relates to a compound which is a specialized pro-resolving lipid mediator as defined herein comprising maresins, D-series resolvins, E-series resolvins, protectins or lipoxins, or a combination thereof, for use in the treatment of neurodegenerative diseases and/or autoimmune diseases.

The present invention further relates to a compound which is a specialized pro-resolving lipid mediator as defined herein selected from the group consisting of maresins, D-series resolvins, E-series resolvins, protectins and lipoxins, or a combination thereof, for use in the treatment of neurodegenerative diseases and/or autoimmune diseases.

In a preferred embodiment, said maresins are maresin-1 or maresin-2; said D-series resolvins are resolvin D1, D2 D3 or D4; said E-series resolvin are resolvin E1 or E2; said protectins are protectin D1 or neuroprotection D1; and said lipoxins are lipoxin A4 or aspirin-triggered lipoxin. In a more preferred embodiment, said specialized pro-resolving lipid mediator for use in the treatment of neurodegenerative diseases and/or autoimmune diseases is a maresin-1 or maresin-2. In the context of the present application, the term "maresin" include maresin-1 and/or maresin-2.

Maresin 1 (7(R)-MaR1) is a 7,14-dihydroxy DHA formed from 14(S)-hydroperoxy DHA supplied exogenously to resident peritoneal mouse macrophages activated with zymosan A. Maresin 2 (MaR2) is a 13R,14S-dihydroxy DHA formed by recombinant human macrophage 12-lipoxygenase and soluble epoxide hydrolase co-incubated with DHA. Resolvin E1 (RvE1) is 5S,12R,18R-trihydroxy-eicosa-6Z,8E,10E,14Z,16E-pentaenoic acid). Resolvin E2 (RvE2) is 5S,18-dihydroxy-eicosa-6E,8Z,11Z,14Z,16E-pentaenoic acid). Protectin D1 (PD1) is 10R,17S-dihydroxy-docosa-4Z,7Z,11E,13E,15Z,19Z-hexaenoic acid). Resolvin D1 (RvD1) is 7S,8R,17S-trihydroxy-docosa-4Z,9E,11E,13Z,15E,19Z-hexaenoic acid). Resolvin D2 (RvD2) is 7S,16R,17S-trihydroxy-docosa-4Z,8E,10Z,12E,14E,19Z-hexaenoic acid). Resolvin D3 (RvD3) is 4S,11R,17S-trihydroxy-docosa-5Z,7E,9E,13Z,15E,19Z-hexaenoic acid). Resolvin D4 (RvD4) is 4S,5,17S-trihydroxy-docosa-6E,8E,10Z,13Z,15E,19Z-hexaenoic acid). Lipoxin A4 (LXA4) is 5S,6R,15S-trihydroxy-eicosa-7E,9E,11Z,13E-tetraenoic acid).

As used herein and defined in the background section "Specialized pro-resolving lipid mediator" (SPM, also termed specialized pro-resolving mediators) are a large and growing class of cell signaling molecules formed in cells by the metabolism of polyunsaturated fatty acids (PUFA) by one or a combination of lipoxygenase, cyclooxygenase, and cytochrome P450 monooxygenase enzymes.

In a particular embodiment, said specialized pro-resolving lipid mediator is in the form of a tautomer, solvate, hydrate, or a pharmaceutically acceptable salt thereof, providing that the chemical structure of these compounds allows to be present in these forms.

"Pharmaceutically acceptable salt" as used herein means that the salt derived from the corresponding compound is suitable for administration to a subject to achieve the treatments described herein, without unduly deleterious side effects in light of the severity of the disease and necessity of the treatment. However, salts of acids and bases which are non-pharmaceutically acceptable may also find use, for example, in the preparation or purification of a pharmaceutically acceptable compound. All salts, whether pharmaceutically acceptable or not are included within the scope of the present invention. The pharmaceutically acceptable acid and base addition salts as mentioned hereinabove are meant to comprise the therapeutically active non-toxic acid and base addition salt forms which the compounds as disclosed herein are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

In another preferred embodiment, said neurodegenerative diseases and/or autoimmune diseases are selected from the group consisting of Multiple Sclerosis, Amyotrophic Lateral Sclerosis, Alzheimer's disease, Parkinson's disease, HIV dementia, epilepsy, schizophrenia, depression, manic depression, neurodevelopmental disorder, autism, stroke, Huntington's disease, inflammatory bowel disease, psoriasis, rheumatoid arthritis and systemic lupus erythematosus. In a more preferred embodiment, said disease is Multiple Sclerosis (MS). In another more preferred embodiment, said disease is Amyotrophic Lateral Sclerosis (ALS).

In another embodiment, the specialized pro-resolving lipid mediator for use, according to any of the preceding embodiments, is included in a composition. In a preferred embodiment, said composition is formulated as a cosmetic composition, pharmaceutical composition, food formula, food ingredient or supplement, functional food, nutritional supplement, nutraceutical composition or is in the extract of a natural product. In a more preferred embodiment, said composition is a pharmaceutical composition. In another more preferred embodiment, said composition is a food.

A composition of a "food" or "food ingredient or supplement", "functional food" or "nutritional supplement" as described above may in principle take any form suited for consumption by man or animal.

In addition, the composition comprising SPMs might contain other ingredients. For example, the composition comprising SPMs are mixed, dissolved, emulsified (e.g., in oil/water, water/oil, or double emulsions), or suspended in a matrix or base. The matrix or base can, e.g., be an edible oil such as ω-3 PUFA-containing oils, an ω-3 PUFA concentrate containing high levels of EPA, or DELA, or mixtures of EPA and DELA, or another edible oil suitable for consumption or administration. The matrix or base might also be water or an aqueous buffer. The composition comprising SPMs might also be prepared in liposomes, nanoparticles, or microparticles.

To enhance shelf life, the compositions might also contain one or more stabilizers including antioxidants such as one or several tocopherols, ascorbic acid and ascorbyl-fatty acid derivatives, and other antioxidants which are commonly used in the stabilization of dietary oils, such as rosemary extract. The composition might furthermore be packaged in containers that minimize exposure to oxygen, heat, and incident light. These conditions will specifically augment the stability of the SPMs by preventing or limiting oxidation and isomerization of double bonds. Stability of the bulk oil or the formulated oil will also benefit from these conditions since the SPMs are dissolved in oils with a significant level of PUFA that are sensitive to oxidation.

The compositions might also include one or more active ingredients such as aspirin, other non-steroidal anti-inflammatory drugs, vitamins, anti-oxidants, flavonoids, minerals, trace elements, fatty acids, lycopene, S-adenosylmethionine, oleocanthal, resveratrol, pterostilbene, bioactive proteins and peptides such as bromelain, oligosaccharides, glucosinolates, and plant extracts such as Boswellia serrata, mangosteen, capsicum, turmeric, ginger, tea, neem, and/or willow bark extract. Ingredients are not limited to the here mentioned examples.

Specific nutritional supplements can be made to support specific health conditions that include a fish oil, a krill oil, or a long-chain ω-3 PUFA concentrate supplemented with a composition comprising SPMs, together with glucosamine and chondroitin for arthritis, or with zinc, lutein and zeaxanthin for eye health.

Other nutritional supplements comprising SPMs are multi-vitamin preparations, sports nutrition, fortified fish oil capsules, oral healthcare products such as tooth paste and mouthwash, and specific oils used as food such as spreads, dressings, cooking oils, snacks, nutritional drinks, soft gels, chewing gums, and in infant formulas.

Nutraceuticals can be defined as natural products that are used to supplement the diet by increasing the total dietary intake of important nutrients. This definition includes nutritional supplements such as vitamins, minerals, herbal extracts, antioxidants, amino acids, and protein supplements. Nutraceutical products fit into the newly created product category of "Dietary Supplements" as established by the F.D.A. in the Dietary Supplement Act of 1994. This act specifically defined dietary supplements to include: vitamins, minerals, herbs or other botanicals, antioxidants, amino acids, or other dietary substances used to supplement the diet by increasing the total daily intake. A "nutraceutical composition" is defined herein as a food composition fortified with ingredients capable of producing health benefits. Such a composition in the context of the present invention may also be indicated as foods for special dietary use; medical foods; and dietary supplements. For example, the food item or supplement may help to prevent or reduce symptoms associated with an inflammatory condition such as allergies (e.g. hay fever) and the like. As with the pharmaceutical composition, the amount of active ingredient in the food or food additive will depend on several factors. The food product will generally comprise a concentration that is sufficient to provide a consumer with an effective amount of active ingredient upon consumption of a regular (e.g. daily) portion of the food product. It will be recognized by those skilled in the art that the optimal quantity and spacing of individual dosages for achieving the therapeutic effects of the pharmaceutical composition, food item or food supplement described herein may easily be determined by the skilled person.

Dose ranges of the pharmaceutical compositions can be adjusted as necessary for the treatment of individual patients and according to the specific condition treated. Any of a number of suitable pharmaceutical formulations may be utilized as a vehicle for the administration of the compositions of the present invention and maybe a variety of administration routes are available. The particular mode selected will depend of course, upon the particular formulation selected, the severity of the disease, disorder, or condition being treated and the dosage required for therapeutic efficacy.

The composition comprising the specialized pro-resolving lipid mediator for use, according to any of the preceding embodiments, is to be administered, but not limited thereto, by oral, rectal, topical, vaginal, parenteral (e.g., subcutaneous, intramuscular, intradermal, inhalation or intravenous), intrathecal, transdermal, intraperitoneal, and intrapulmonary and intranasal route. Preferably, said composition is to be administered by oral or parenteral route, although the most suitable route in any given case will depend on the nature and severity of the condition being treated and on the nature of the particular active product used.

Formulations suitable for oral administration may be presented in discrete units, such as capsules, cachets, lozenges, drops, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, inhalational or intradermal injection. Such preparations may conveniently be prepared by admixing the compound with water or a glycine buffer and rendering the resulting solution sterile and isotonic with the blood.

Formulations of the present invention are particularly suitable for topical application to the skin and preferably take the form of an ointment, cream, lotion, paste, gel, spray, aerosol, or oil. Carriers which may be used include Vaseline, lanoline, polyethylene glycols, alcohols, transdermal enhancers, and combinations of two or more thereof.

Formulations suitable for transdermal administration may also be presented as medicated bandages or discrete patches adapted to remain in intimate contact with the epidermis of the recipient for a prolonged period of time. Formulations suitable for transdermal administration may also be delivered by iontophoresis (passage of a small electric current to "inject" electrically charged ions into the skin; also called electromotive drug administration (EMDA)) through the skin.

The present disclosure also relates to a method of treatment of neurodegenerative diseases and/or autoimmune diseases, as defined above, in a subject comprising administering to said subject a therapeutically effective amount of a specialized pro-resolving lipid mediator, as defined above. Preferably, the subject is a human subject. In addition, the present invention also relates to a method of treatment of neurodegenerative diseases and/or autoimmune diseases, as defined above, in a subject comprising administering to said subject a therapeutically effective amount of a composition comprising a specialized pro-resolving lipid mediator, as defined above. The phrase "therapeutically effective amount" means the amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present disclosure may be administered in a sufficient amount to produce a reasonable benefit/risk ratio applicable to such treatment.

It should be noted that all the previous embodiments can be practiced independently from each other or combined with any other embodiment disclosed herein.

The present invention will be now further illustrated by reference to the following examples which do not intend to limit the scope of the present invention.

EXAMPLES

Example 1: Experimental Autoimmune Encephalomyelitis (EAE), Multiple Sclerosis (MS) Mouse Model EAE Induction and Functional Assessment Active immunization was done in female adult (8 weeks old) C57Bl/6 mice. Briefly, were subcutaneously injected with 300 pg of myelin oligodendrocyte glycoprotein $(MOG)_3$5-55 peptide (MEVGWYRSPFSRVVHLYRNGK; SEQ ID NO:1) emulsified in complete Freund's Adjuvant supplemented with 4 mg of *Mycobacterium tuberculosis* H37RA (DIFCO Laboratories).

Results

We found that mice showed the first signs of disease between day 10-13 post-immunization (FIG. 1A). Functional deficits progressed in saline-injected mice over time, reaching a plateau by day 18 post-immunization. At this time point, saline-injected mice had a clinical score of ~4.5, which indicates paralysis of both hind limbs and weakness in front limbs (FIG. 1A). This score did not vary until the end of the follow up. Interestingly, administration of Maresin resulted in marked amelioration of functional disabilities, showing a clinical score of ~2.5 at the peak of disease (FIG. 1A). This score indicates that mice did not show hind limb paralysis, although they displayed slight or severe weakness of hindlimbs but not in forelimbs. Histopathological sections of the spinal cords also revealed that Maresin treatment reduced in ~50% the area of demyelination as compared to those mice treated with saline (FIG. 1B). This data provide clear evidence that Maresin treatments confers protections against functional and myelin loss in a preclinical model of multiple sclerosis.

Example 2: Amyotrophic Lateral Sclerosis

Animals

Experiments were performed in female transgenic mice carrying the G93A human SOD1 mutation (B6-Tg[SOD1-G93A]1Gur) obtained from the Jackson Laboratory (Bar Harbor, Me., USA) and provided from the colony maintained at the University of Zaragoza. Hemizygous transgenic mice were identified by PCR amplification of DNA extracted from tail samples and then were maintained in local facilities. Mice were housed with food and water ad libitum at room temperature of 22±2° C. under a 12:12-h light-dark cycle. It was considered that animals reached the endpoint of the disease when the righting reflex was lost for longer than 30 s. At 8 weeks of age (prior to the beginning of the treatment), animals were electrophysiologically tested to obtain baseline levels. Animals were then distributed among the different experimental groups according to their progenitors, weight and electrophysiology baseline values in balanced groups, either Maresin-treated or saline—SOD1$^{G93A}$ mice. Administration of Maresin was done intraperitoneally (1 µg in 200 µl saline) on Monday, Wednesday and Friday, starting at the age of 8 weeks.

Functional Tests

Motor coordination, balance and strength of the animals were assessed using the Rotarod test 20. All mice were trained three times a week on the rod rotating at constant speed of 14 rpm (rotating cylinder 3.4 cm diameter) for a maximum of 180 seconds to reach the baseline level of performance. Animals were then tested weekly from 8 until 16 weeks of age at the same speed, and the time for which each animal could remain on the rotating rod was measured. An arbitrary maximum time of remaining on the rotating rod of 180 s was considered.

Motor nerve conduction tests were performed every 2 weeks from 8 weeks to 20 weeks of age (n=12 SOD1$^{G93A}$ vehicle, n=13 SOD$^{G93A}$ treated with Maresin). The sciatic nerve was percutaneously stimulated through a pair of needle electrodes placed at the sciatic notch, by means of single pulses of 0.02 ms duration (Grass S88). The compound muscle action potential (CMAP, M-wave) was recorded from the tibialis anterior (TA). All potentials were amplified and displayed on a digital oscilloscope (Tektronix 450S) at settings appropriate to measure the amplitude from baseline to the maximal negative peak. The recording needles were placed using a microscope and guided by anatomical landmarks, to ensure reproducibility of needle location on all animals. During the tests, the mouse skin temperature was maintained between 34 and 36° C. using a thermostatically controlled heating pad. All the evaluators were blinded to the experimental groups.

Results

Figures 2A, 2B:
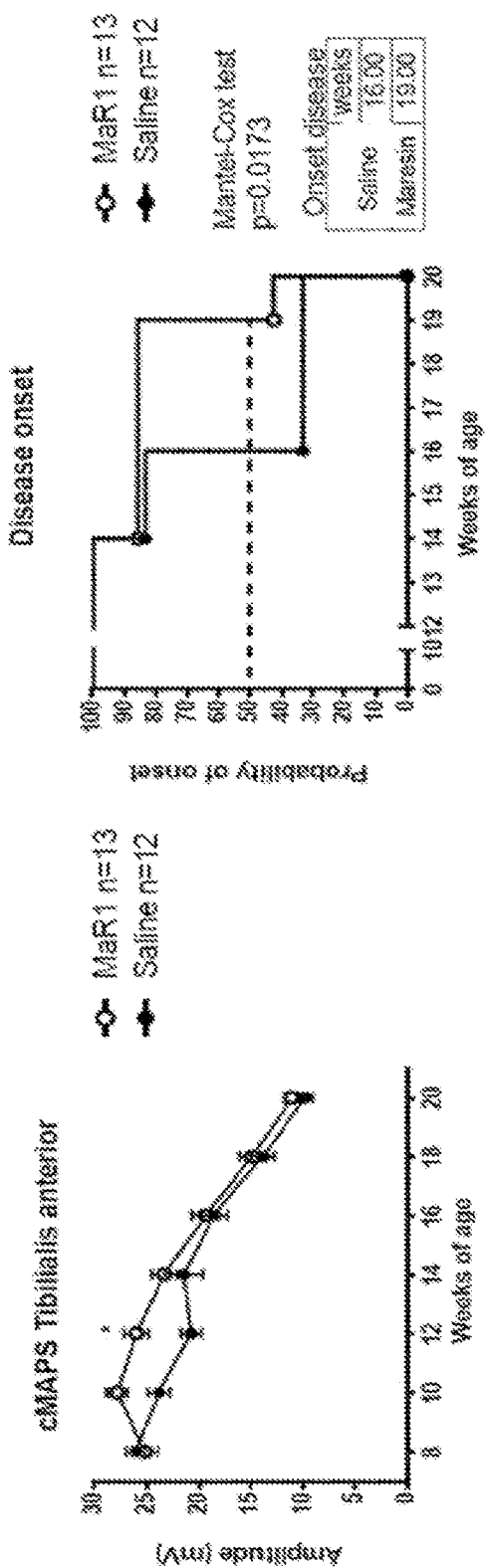
FIG. 2A and FIG. 2B show that administration of Maresin confers significant protection against functional loss in ALS.

We found that neuro-muscular integrity of tibialis anterior muscles assessed electrophysiologically by doing compound muscle action potentials (CMAP) decreased progressively in the SOD1$^{G93A}$ from 8 weeks of age until the week 20 mice (FIG. 2A). Nevertheless, the first signs of gross motor loss assessed in the rotarod test were observed at week 14, although the median disease onset in saline treated ALS mice was 16 weeks (FIG. 2B). Interestingly, treatment with Maresin delayed electrophysiological loss in about 4 weeks (FIG. 2A). In line with the electrophysiological data, we observed that Maresin treatment also delayed of disease onset based on the rotarod test in 3 weeks (median disease onset was 19 weeks) (FIG. 2B). These data provide clear evidence that Maresin provide significant therapeutic effects in a mouse model of ALS.

In the specification and in the claims, the terms "including" and "comprising" are open-ended terms and should be interpreted to mean "including, but not limited to . . . ". These terms encompass the more restrictive terms "consisting essentially of" and "consisting of". It must be noted that as used herein and in the appended claims, the singular forms "a", "an", and "the" include plural reference unless the context clearly dictates otherwise.

Example 3: Experimental Autoimmune Encephalomyelitis (EAE), Multiple Sclerosis (MAs) Mouse Model in Oral Treatment EAE Induction and Functional Assessment Active immunization was done in female adult (8 weeks old) C57Bl/6 mice. Briefly, were subcutaneously injected with 300 pg of myelin oligodendrocyte glycoprotein (MOG)$_3$5-55 peptide (MEVGWYRSPFSRVVHLYRNGK; SEQ ID NO:1) emulsified in complete Freund's Adjuvant supplemented with 4 mg of *Mycobacterium tuberculosis* H37RA (DIFCO Laboratories). On day 0 and 2, the mice were also injected intraperitoneally (i.p.) with 500 ng of pertussis toxin (List Biological Laboratories). Animals were monitored daily for signs of EAE and the scoring system is as follows: 0=no clinical symptoms; 0.5=partial floppy tail, 1=floppy tail; 2=mild hind-limb weakness (quick righting reflex); 3=severe hind-limb weakness (slow righting reflex); 3.5=weakness in hind limbs or paralysis of one hind limb; 4=paralysis of both hind limbs, 4.5=weakness in front limbs; 5=paralysis of front limbs; 6=moribund. Once the animals showed the first signs of disease, mice received daily oral treatment of Maresin (1 µg in 200 µl of saline) until the end of the experiment (day 21 postimmunization). Control mice received 200 µl of saline following the same treatment protocol.

Results

Figure 3:
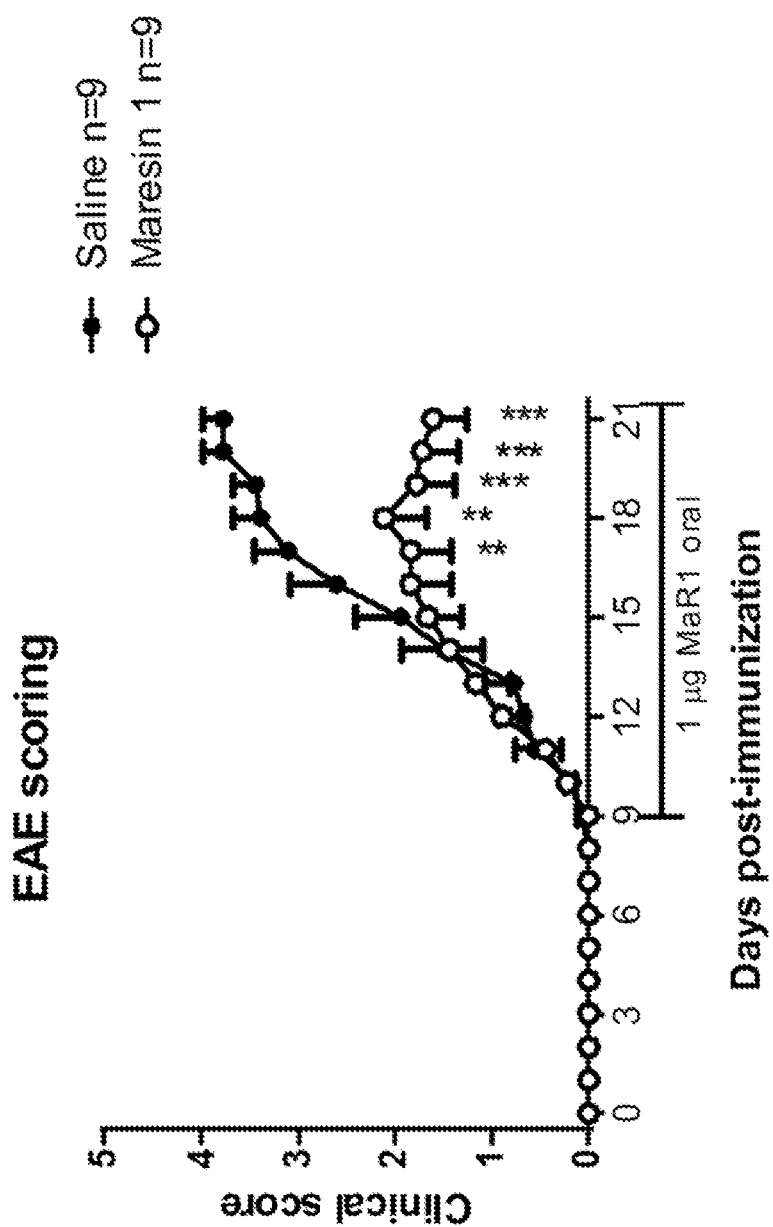
FIG. 3 shows the therapeutic effects of oral Maresin in an Experimental Autoimmune Encephalomyelitis (EAE), a mouse model of multiple sclerosis. via the assessment of locomotor loss in EAE mice over time. Note that treatment with Maresin at disease onset led to significant amelioration of locomotor deficits (*p<0.05 vs vehicle; Two-way repeated measurements ANOVA with Bonferroni post-hoc test).

We found that mice showed the first signs of disease between day 9-12 post-immunization (FIG. 3). Functional deficits progressed in saline-injected mice over time, reaching a plateau by day 20 post-immunization. At this time point, saline-injected mice had a clinical score of ~4, which indicates paralysis of both hind limbs (FIG. 3). This score did not vary until the end of the follow up. Interestingly, oral administration of Maresin resulted in marked amelioration of functional disabilities, showing a clinical score of ~2.5 at the peak of disease (FIG. 3). This score indicates that mice did not show hind limb paralysis, although they displayed slight or severe weakness of hindlimbs.

The invention claimed is:

1. A method of treating a neurodegenerative disease or an autoimmune disease in a subject in need thereof comprising administering a therapeutically effective amount of a composition comprising at least one isolated maresin to the subject, wherein the administration of the composition to the subject reduces (a) locomotor loss, (b) demyelination, (c) paralysis, or (d) a combination thereof.

2. The method according to claim 1, wherein the maresin is maresin-1, maresin-2, or a combination thereof.

3. The method according to claim 1, wherein the neurodegenerative disease is selected from the group consisting of amyotrophic lateral sclerosis (ALS), Parkinson's disease, Huntington's disease, and Alzheimer's disease.

4. The method according to claim 1, wherein the autoimmune disease is multiple sclerosis.

5. The method according to claim 1, wherein the composition is formulated as a pharmaceutical composition.

6. The method according to claim 1, wherein the composition is formulated as a food, functional food, food ingredient or supplement, nutritional supplement, nutraceutical composition or medical food or is in the extract of a natural product or cosmetic composition.

7. The method according to claim 1, wherein the composition is administered by oral, intravenous, subcutaneous, intramuscular, rectal, topical, vaginal, parenteral, transdermal, intraperitoneal, intrapulmonary, intrathecal or intranasal route.

8. A method of treating, preventing, or reducing neurodegeneration in a subject comprising administering a therapeutically effective amount of a composition comprising at least one isolated maresin to the subject, wherein the administration of the composition treats, prevents, or reduces neurodegeneration in a subject.

9. The method according to claim 8, wherein the maresin is maresin-1, maresin-2, or a combination thereof.

10. The method of claim 8, wherein the administration of the composition to the subject reduces (a) locomotor loss, (b) demyelination, (c) paralysis, or (d) a combination thereof.

11. The method according to claim 8, wherein the neurodegeneration is due to a neurodegenerative disease or an autoimmune disease.

12. The method according to claim 11, wherein the neurodegenerative disease is selected from the group consisting of amyotrophic lateral sclerosis (ALS), Parkinson's disease, Huntington's disease, and Alzheimer's disease.

13. The method according to claim 11, wherein autoimmune disease is multiple sclerosis.

14. The method according to claim 8, wherein the composition is formulated as a pharmaceutical composition.

15. The method according to claim 8, wherein the composition is formulated as a food, functional food, food ingredient or supplement, nutritional supplement, nutraceutical composition or medical food or is in the extract of a natural product or cosmetic composition.

16. The method according to claim 8, wherein the composition is administered by oral, intravenous, subcutaneous, intramuscular, rectal, topical, vaginal, parenteral, transdermal, intraperitoneal, intrapulmonary, intrathecal or intranasal route.

17. A method of treating ALS in a subject in need thereof comprising administering to the subject a therapeutically neuroprotective effective amount of a composition comprising isolated maresin-1.

18. The method of claim 17, wherein the administration of the composition to the subject reduces (a) locomotor loss, (b) demyelination, (c) paralysis, or (d) a combination thereof.

19. The method according to claim 17, wherein the composition is formulated as a pharmaceutical composition.

20. The method according to claim 17, wherein the composition is formulated as a food, functional food, food ingredient or supplement, nutritional supplement, nutraceutical composition or medical food or is in the extract of a natural product or cosmetic composition.

21. The method according to claim 17, wherein the composition is administered by oral, intravenous, subcutaneous, intramuscular, rectal, topical, vaginal, parenteral, transdermal, intraperitoneal, intrapulmonary, intrathecal or intranasal route.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: MOG35-55

-continued

```
<400> SEQUENCE: 1

Met Glu Val Gly Trp Tyr Arg Ser Pro Phe Ser Arg Val Val His Leu
1               5                   10                  15

Tyr Arg Asn Gly Lys
            20
```